United States Patent [19]
Pfaff et al.

[11] Patent Number: 5,919,236
[45] Date of Patent: Jul. 6, 1999

[54] JOINT PROSTHESIS

[75] Inventors: Hans-Georg Pfaff, Ostfildern; Hartmut Kalberer, Deizisau, both of Germany

[73] Assignee: Cerasiv GmbH - Innovatives Keramik Engineering, Plochingen, Germany

[21] Appl. No.: 08/916,670

[22] Filed: Aug. 22, 1997

[30] Foreign Application Priority Data

Aug. 24, 1996 [DE] Germany .............................. 196 34 274
Jan. 17, 1997 [DE] Germany .............................. 197 01 536

[51] Int. Cl.⁶ ........................................................ A61F 2/34
[52] U.S. Cl. ............................................................... 623/22
[58] Field of Search ................................. 623/16, 18, 22, 623/23

[56] References Cited

U.S. PATENT DOCUMENTS

| | | | |
|---|---|---|---|
| 4,012,795 | 3/1977 | Dorre et al. ................................. | 623/23 |
| 4,058,856 | 11/1977 | Doerre et al. . | |
| 4,822,367 | 4/1989 | Stuhmer . | |
| 4,964,869 | 10/1990 | Auclair et al. .............................. | 623/22 |
| 5,108,447 | 4/1992 | Zeiler et al. . | |
| 5,310,408 | 5/1994 | Schryver et al. ........................... | 623/22 |
| 5,362,311 | 11/1994 | Amino et al. ............................... | 623/22 |
| 5,405,392 | 4/1995 | Deckner ..................................... | 623/22 |
| 5,413,603 | 5/1995 | Noiles et al. ............................... | 623/22 |
| 5,413,610 | 5/1995 | Amino et al. . | |
| 5,458,649 | 10/1995 | Spotorno et al. . | |
| 5,507,828 | 4/1996 | Maumy et al. . | |
| 5,549,703 | 8/1996 | Daigle et al. ............................... | 623/23 |
| 5,609,647 | 3/1997 | Kalberer et al. . | |

FOREIGN PATENT DOCUMENTS

| | | | |
|---|---|---|---|
| 0144588 | 6/1985 | European Pat. Off. .................. | 623/22 |
| 0237751 | 9/1987 | European Pat. Off. .................. | 623/22 |
| 237751 | 9/1987 | European Pat. Off. . | |
| 444381 | 9/1991 | European Pat. Off. . | |
| 445068 | 9/1991 | European Pat. Off. . | |
| 586335 | 3/1994 | European Pat. Off. . | |
| 640324 | 3/1995 | European Pat. Off. . | |
| 649641 | 4/1995 | European Pat. Off. . | |
| 694294 | 1/1996 | European Pat. Off. . | |
| 2329249 | 5/1977 | France . | |
| 2548591 | 10/1975 | Germany . | |
| 4337936 | 5/1995 | Germany . | |
| 9423670 | 10/1994 | WIPO . | |

*Primary Examiner*—David J. Isabella
*Attorney, Agent, or Firm*—Antonelli, Terry, Stout & Kraus, LLP

[57] ABSTRACT

Joint prosthesis (1) with a cup-shaped supporting part (2) in whose interior a ceramic insert (3) is fastened by conical clamping. Clamping surface (6) of insert (3) runs at an angle (α) to clamping surface (7) of supporting part (2).

14 Claims, 2 Drawing Sheets

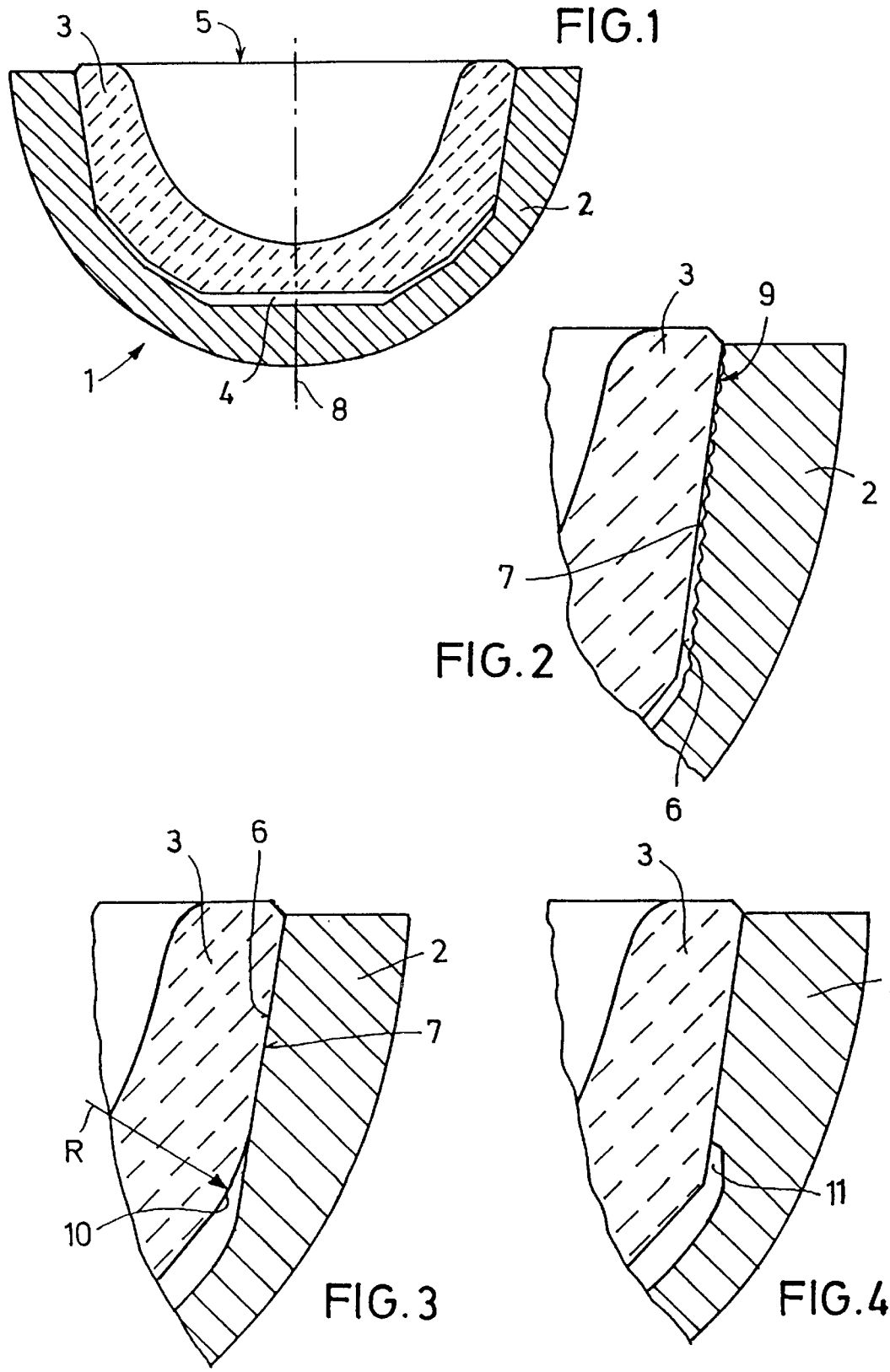

JOINT PROSTHESIS

BACKGROUND OF THE INVENTION

The present invention relates to a joint prosthesis with a cup-shaped supporting part in which a ceramic insert is secured by a conical clamp.

Joint prostheses are known that have a metallic supporting part and an insert contained therein. The metallic supporting part is anchored in the bone of the patient. The insert forms a wear-resistant sliding surface against which the joint ball of the bone or another joint prosthesis presses. In so-called hard-sliding pairs, at least one part of the joint connection, the insert for example, is made of metal. The fastening of the metal insert in the supporting part which likewise consists of metal is performed with the aid of a polyethylene coupling. The polyethylene coupling is subjected to wear by microrelative movements. This wear is not so serious as frictional wear but the seat of the insert is loosened and abrasion enters the tissue and acetabulum.

U.S. Pat. No. 5,282,864 describes a joint prosthesis in which a metal insert is anchored in a metal supporting part by screws. The insert consists of a cobalt-chromium alloy while the supporting part is made of a titanium alloy. As a result of this design for the joint prosthesis, there is a risk of frictional corrosion and galvanic corrosion. During corrosion, the metals give off toxic ions that can harm the patient.

To overcome these disadvantages, ceramic inserts are used in the metallic supporting parts. Since ceramic materials can be machined only with difficulty, they are usually fastened in the supporting part by conical clamping. An example of this is described in EP 0 649 641 A2.

During conical clamping, considerable tensile stresses develop in certain zones of the insert because the initiation of force cannot be controlled. Although ceramic materials are very hard and resistant to compression, they can accept tensile forces to only a limited degree. This means that thin-walled ceramic inserts in particular cannot be made for technical reasons.

SUMMARY OF THE INVENTION

The invention is based on the goal of designing the connection between the supporting part and the insert in such fashion that a reliable, reproducible connection is produced and the insert can also be prevented from coming loose.

This goal is achieved according to the present invention.

In the joint prosthesis according to the invention, the ceramic insert is fastened by conical clamping in the cup-shaped supporting part. The angle of the clamping surface of the insert is different from the angle of the clamping surface of the supporting part, so that the insert is connected to the supporting part over only a relatively small area. This permits a controlled transmission of force from the insert to the supporting part. The joint force that acts axially is applied to a large extent in compressive stresses that act circumferentially so that the development of tensile stresses during use is minimized.

In one preferred embodiment of the invention, the connection between the supporting part and the insert is provided in the area of the opening side of the joint prosthesis. At the end that faces away from the opening side, the clamping surfaces do not touch one another. This has the advantage that the force to be accepted by the joint prosthesis is initiated in a certain area distributed uniformly around the circumference.

The load-bearing surface of the supporting part can be roughened so that a roughness of 20 $\mu$m is produced for example. In this way, irregularities in force transmission, resulting for example from variations in shape in the micro range, can be avoided.

To improve the frictional properties, the clamping surface of the supporting part can be precision-turned or ground so that the surface has a roughness of 0 to 4 $\mu$m.

Preferably, the insert has a radius or a slight additional bevel at the end of the clamping surface that faces away from the opening side. As a result, tilting of the insert when it is inserted or when subjected to load is prevented. This can also be achieved by having a relief groove adjoin the end of the clamping surface of the supporting part that faces away from the opening side.

As the insert wears, it must be replaced. In order to minimize the stress on the patient, the insert is removed in situ from the supporting part, while the supporting part remains in the bone. In order to be able to remove the insert easily, in a special design of the invention at least one recess is provided that extends from the opening side on the boundary surface between the insert and the supporting part, up to the ends of the two clamping surfaces away from the opening side. At the inner end of the recess that faces away from the opening side there is a tilting lever that fits behind the clamping surface of the insert. By means of a tool, such as a wedge for example, the end of the tilting lever that is in the recess can be pressed against the insert, and the latter removed from the supporting part.

BRIEF DESCRIPTION OF THE DRAWINGS

Embodiments of the invention are described in greater detail below with reference to the drawings.

FIG. 1 is a section through a joint prosthesis with a supporting part and an insert secured therein;

FIG. 2 is a detailed view of the conical clamp;

FIG. 3 is a detailed view of the internal end of the clamping surface of the insert;

FIG. 4 is a detailed view of the inner end of the clamping surface of the supporting part;

DETAILED DESCRIPTION OF THE PREFERRED EMBODIMENTS

Figure 5:
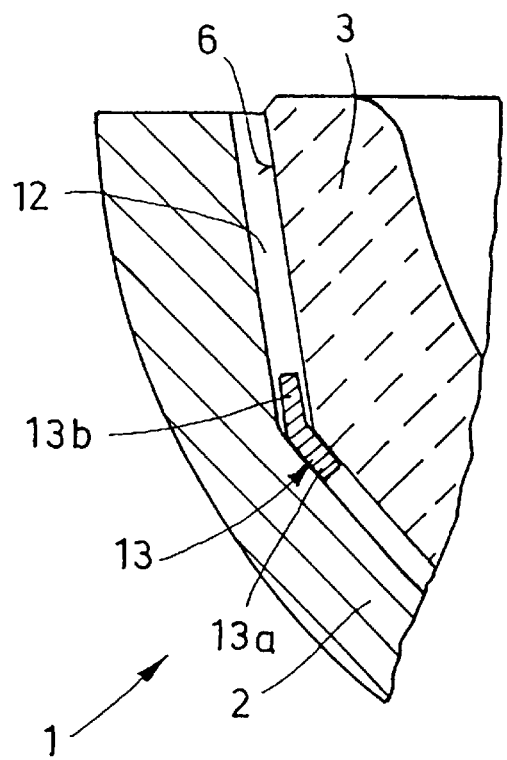
FIG. 5 is a detailed view of the joint prosthesis with a recess and with a tilting lever located therein for releasing the insert.

FIG. 1 shows a joint prosthesis 1 consisting of a cup-shaped metallic supporting part 2 and a ceramic insert 3 that forms the artificial acetabulum. Insert 3 is located in an interior chamber 4 of supporting part 2. The inner surface of insert 3 is designed as a spherical cup that receives the matching part of the joint on opening side 5. Insert 3 is secured in supporting part 2 by conical clamping.

Clamping surface 6 of insert 3 runs at an angle $\alpha$ to clamping surface 7 of supporting part 2 (FIG. 2). The angle at which insert clamping surface 6 runs to joint axis 8 of the joint prosthesis is larger than the angle of the supporting part clamping surface 7.

This means that insert 3 is pressed against supporting part 2 over only a relatively small contact area 9 that is located on opening side 5. The size of contact area 9 can be modified by changing angle $\alpha$. The smaller the value of angle $\alpha$, the larger contact area 9 will be. Angle α can also be negative. In this case, contact area 9 is located in the lower area of clamping surfaces 6 and 7. The gap between the two contact surfaces 6 and 7 therefore opens to opening side 5.

Clamping surface 7 of supporting part 2 has a roughness of about 20 μm. As a result, compensation is provided for variations in the shape of insert 3.

In FIGS. 3 and 4, clamping surfaces 6 and 7 are shown parallel to one another and not roughened, in order to improve clarity. In fact, however, the connection between insert 3 and supporting part 2 is as shown in FIG. 2. In FIG. 3 a curved surface 10 with radius R abuts the lower end area of clamping surface 6 of insert 3. When insert 3 is introduced into supporting part 2, this rounding of the lower edge of clamping surface 6 avoids tilting of insert 3 in supporting part 2. This can also be achieved by providing a relief groove 11 in supporting part 2 which is located in the vicinity of the lower end of clamping surface 6 of supporting part 3 (FIG. 4).

FIG. 5 shows another embodiment of joint prosthesis 1. Supporting part 2 has an elongated recess 12 that is located in the boundary area between supporting part 2 and insert 3 and runs parallel to clamping surface 6 of insert 3. Recess 12 is open to opening side 5 of joint prosthesis 1. At the lower end of the recess is a tilting lever 13 consisting of two legs 13a and 13b that are arranged with respect to one another at a shallow angle. Leg 13a fits behind clamping surface 6 of insert 13 and is clamped between insert 3 and supporting part 2. Second leg 13b extends into recess 12. The angle between the two legs 13a and 13b is made such that second leg 13b runs approximately parallel to recess 12.

Figure 6:
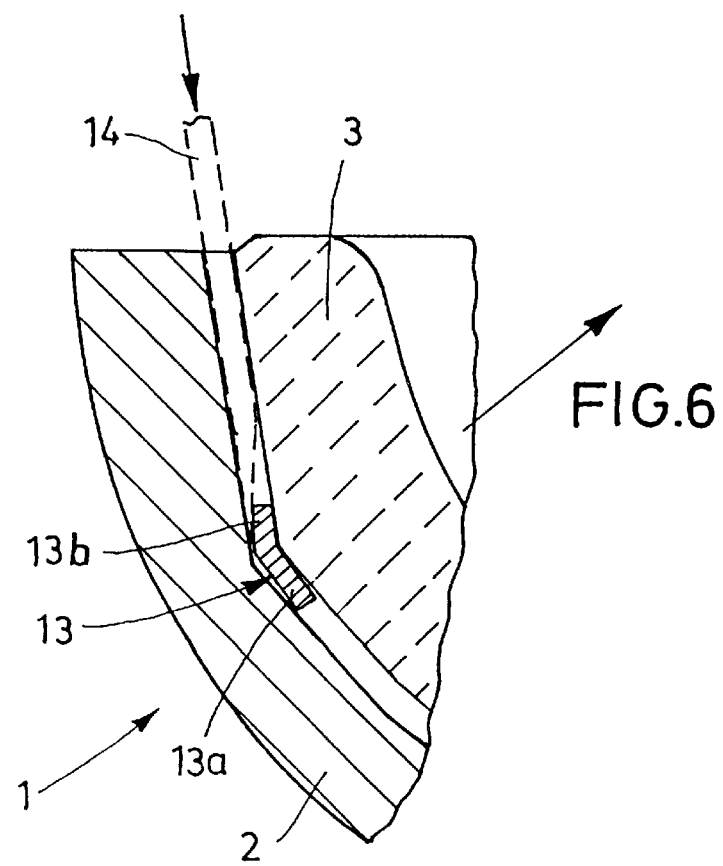
FIG. 6 is a detailed view of the joint prosthesis with a tool for activating the tilting lever.

FIG. 6 shows how tilting lever 13 is activated with the aid of a wedge-shaped tool 14. Wedge 14 is pushed into recess 12 until the tip of the wedge is between supporting part 2 and second leg 13b of tilting lever 13. Applying additional pressure to wedge 14 presses second leg 13b in the direction of insert 3. This also causes first leg 13a to move, pushing insert 3 out of supporting part 2.

We claim:

1. Joint prosthesis comprising a cup-shaped supporting part and a ceramic insert, the insert having an outer clamping surface configured to be inserted within the supporting part, the insert being secured to the supporting part by conical clamping of the outer clamping surface of the insert with an inner clamping surface within the supporting part, wherein an angle between a joint axis and the outer clamping surface of the insert is different from an angle between the joint axis and the inner clamping surface of the supporting part.

2. Joint prosthesis according to claim 1, wherein the outer clamping surface of the insert runs at an angle (α) of 1 to 20 angle minutes relative to the inner clamping surface of the supporting part.

3. Joint prosthesis according to claim 2, wherein the outer clamping surface of the insert abuts the inner clamping surface of the supporting part in the vicinity of an open end of the supporting part to produce conical clamping.

4. Joint prosthesis according to claim 1, wherein the inner clamping surface of the supporting part is roughened.

5. Joint prosthesis according to claim 4, wherein the inner clamping surface of the supporting part has a roughness of 20 μm.

6. Joint prosthesis according to claim 1, wherein the inner clamping surface of the supporting part is smooth.

7. Joint prosthesis according to claim 1, wherein the inner clamping surface of the supporting part has a roughness up to 4 μm.

8. Joint prosthesis according to claim 1, wherein an area of the outer clamping surface at an end having a smaller diameter has a radius (R) that prevents tilting when the insert is inserted into the supporting part.

9. Joint prosthesis according to claim 1, wherein the supporting part has a relief groove at an area of the inner clamping surface that faces a closed end of the supporting part.

10. Joint prosthesis according to claim 1, wherein the supporting part is provided with at least one recess on the inner clamping surface which runs from an open side to a closed end of the supporting part, and wherein a tilting lever is located at an inner end of the at least one recess, said tilting lever fitting behind the outer clamping surface of the insert, wherein the tilting lever can be shifted by a tool to release the insert from the supporting part.

11. Joint prosthesis according to claim 1, wherein the outer clamping surface of the insert runs at an angle (α) of 1 to 5 angle minutes relative to the inner clamping surface of the supporting part.

12. Joint prosthesis according to claim 1, wherein an area of the outer clamping surface at an end having a smaller diameter has a right additional bevel that prevents tilting when the insert is inserted into the supporting part.

13. Joint prosthesis according to claim 1, wherein the angle between the joint axis and the outer clamping surface of the insert is larger than the angle between the joint axis and the inner clamping surface of the supporting part, whereby a single conical clamping area is achieved in a vicinity of an open end of the supporting part.

14. Joint prosthesis according to claim 1, wherein the angle between the joint axis and the outer clamping surface of the insert is smaller than the angle between the joint axis and the inner clamping surface of the supporting part, whereby a single conical clamping area is achieved in a vicinity of an closed end of the supporting part.

* * * * *